(12) United States Patent
Nadiri et al.

(10) Patent No.: US 10,041,986 B2
(45) Date of Patent: Aug. 7, 2018

(54) BALANCED BRIDGE

(71) Applicant: VAYYAR IMAGING LTD, Yehud (IL)

(72) Inventors: Zlvi Nadiri, Mishmar David (IL); Shay Moshe, Petah-Tikva (IL)

(73) Assignee: VAYYAR IMAGING LTD., Yehud (IL)

( * ) Notice: Subject to any disclaimer, the term of this patent is extended or adjusted under 35 U.S.C. 154(b) by 114 days.

(21) Appl. No.: 14/697,493

(22) Filed: Apr. 27, 2015

(65) Prior Publication Data
US 2015/0323577 A1    Nov. 12, 2015

Related U.S. Application Data

(60) Provisional application No. 61/984,812, filed on Apr. 27, 2014.

(51) Int. Cl.
  *G01R 27/06*  (2006.01)
  *G01N 22/00*  (2006.01)
  *G01R 35/00*  (2006.01)
  *G01R 31/28*  (2006.01)

(52) U.S. Cl.
  CPC ............ *G01R 27/06* (2013.01); *G01N 22/00* (2013.01); *G01R 31/2822* (2013.01); *G01R 35/005* (2013.01)

(58) Field of Classification Search
  USPC .......... 324/637, 629, 600, 601, 750.02, 329, 324/638, 750.01, 76.11, 537, 648, 649, 324/651, 706, 76.12, 98; 455/78, 69; 257/E21.521, 48; 702/117, 66, 85; 710/106
  See application file for complete search history.

(56) References Cited

U.S. PATENT DOCUMENTS

| | | | |
|---|---|---|---|
| 2004/0153265 A1* | 8/2004 | Martens et al. ..... | G01R 35/005 702/65 |
| 2008/0191712 A1* | 8/2008 | Eisenstadt et al. .......................... | G01R 31/2884 324/638 |
| 2008/0204041 A1* | 8/2008 | Anderson et al. ..... | G01R 27/28 324/629 |
| 2010/0102829 A1* | 4/2010 | Azarian ................ | G01R 27/28 324/651 |

* cited by examiner

*Primary Examiner* — Melissa Koval
*Assistant Examiner* — Nasima Monsur
(74) *Attorney, Agent, or Firm* — Browdy and Neimark, PLLC (57) ABSTRACT

A directional bridge for characterizing a signal reflected from an RF device under test (DUT) the bridge comprising: a differential signal source with two antipodal outputs wherein the first output is connected to a reference termination, and the second output is connected to the DUT, and at least one equal-ratio resistive divider wherein one side of the resistive divider is attached to the first output, and the second side of the resistive divider is connected to the second output and the middle point of the resistive divider is connected to a receiver, wherein the at least one equal-ratio resistive divider is configured to provide a separated forward and reverse signals by canceling a differential mode of a transmitted signal at the bridge.

4 Claims, 13 Drawing Sheets

BALANCED BRIDGE

FIELD OF THE INVENTION

The present invention relates to the field of test bridges for network analyzers, more particularly to a balanced bridge in a vector network analyzer.

BACKGROUND INFORMATION

A vector network analyzer (VNA) is a useful instrument for many applications where electrical and/or microwave measurements, such as transmission and reflection properties, are needed. VNA's are usually used where the electrical signals have a high frequency, ranging from (but not limited to) 10 kHz to 100 GHz. Since a VNA can be used to measure complex impedances of circuits at high frequencies, VNAs can be found in many electronic and radio frequency (RF) laboratories, as well as in chip/microwave device or system manufacturing facilities.

A VNA can apply a stimulus sine wave to a device under test (DUT) and perform a series of measurements and calculations. VNAs are often used to characterize two-port networks such as amplifiers and filters, but they can be used on networks with an arbitrary number of ports. A two-port VNA can measure both reflected signals from the DUT and transmitted signals through the DUT. Additionally, the VNA can calculate S-parameters and other related parameters for that DUT. The VNA can repeat this procedure using different frequencies and/or power levels to measure the desired characteristics of the DUT.

Figure 1:
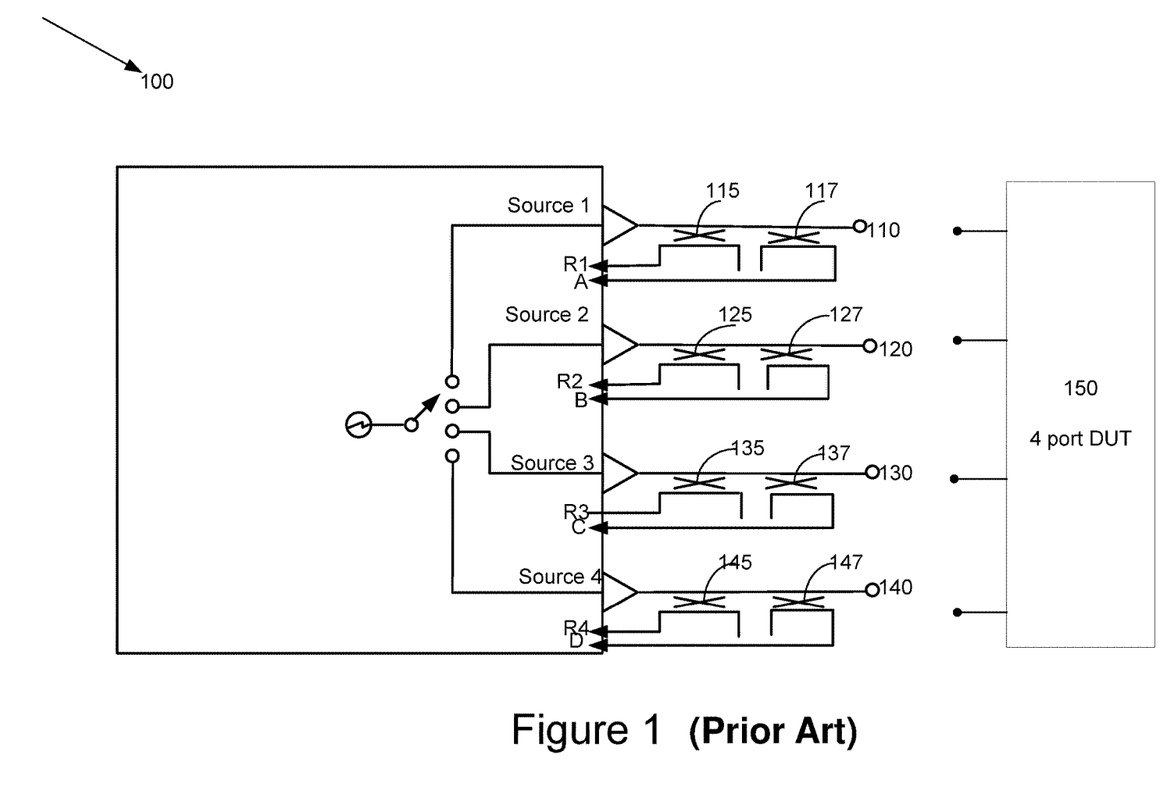
FIG. 1—shows a simplified block diagram of an RF vector network analyzer test set according to the prior art.

The basic architecture of the VNA includes a signal generator, a test set, one or more receivers and a display. A traditional VNA test set 100, as shown in FIG. 1, may include four ports (110, 120, 130 and 140) which may be connected, for example to the DUT ports 150. Each of the test unit ports may be connected to a source transmitter and requires two directional couplers which are connected to two receivers for measuring the reference signal (i.e. R1, R2, R3 and R4) and the received signals (i.e. A, B, C and D). Therefore, according to the prior art solution two receivers are required for each test port. The traditional VNA further includes a number of switches and couplers, such as couplers 115, 117, 125, 127, 135, 137, 145 and 147 located on each branch of the VNA test set 100. The couplers are configured to sample, measure and direct the transmit signal (forward) and the return signals (backward direction) at the VNA (for each direction a single coupler is needed).

The receivers and the transmitters at the VNA are synchronized according to methods known in the field. The testing may be performed simultaneously on all the VNA's ports or separately and alternately at each port.

As illustrated in FIG. 1 the traditional VNA is a complex device which typically occupies a large space, includes multiple elements (such as switching elements connectors and couplers) and is expensive. Moreover, some of the elements are mechanical elements (i.e. coaxial switches) that must be frequently switched, resulting in the decrease of the traditional VNA's reliability.

Figure 2:
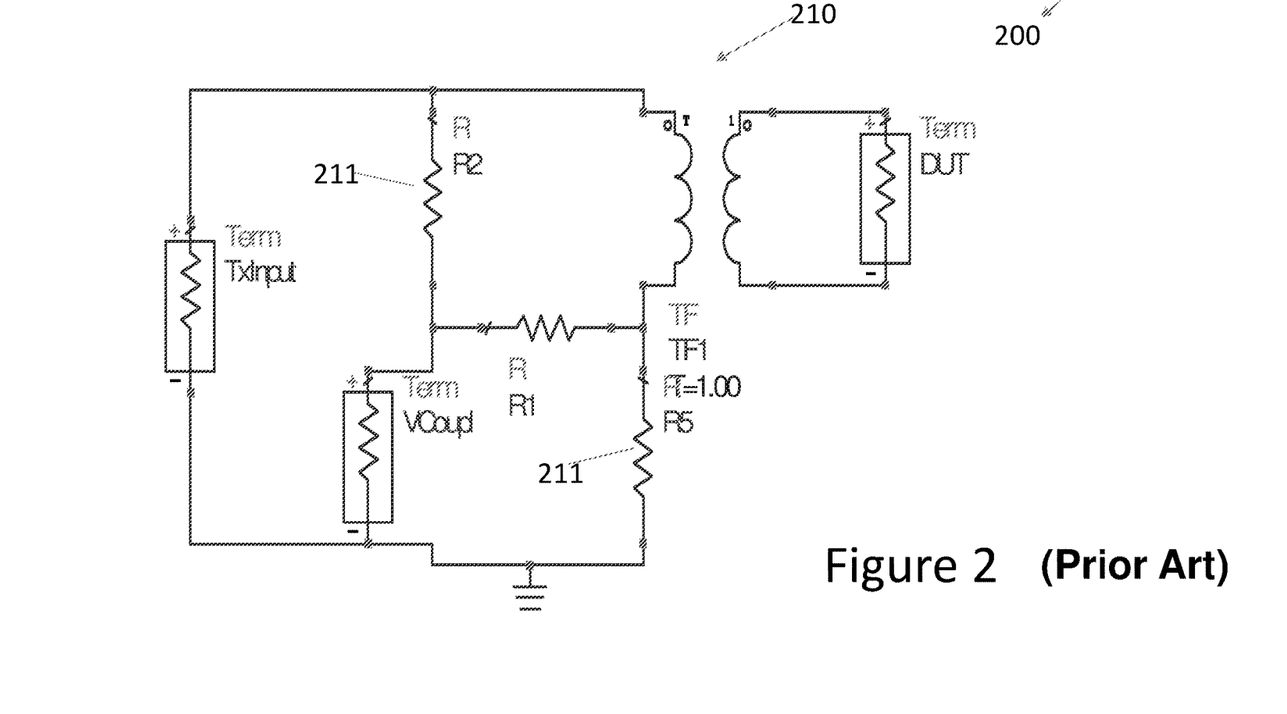
FIG. 2—shows a simplified block diagram of a conventional basic measurement bridge, constructed according to the principles of the prior art.

The prior art solutions that are currently used to overcome such problems, rely on either utilizing many couplers and receivers as shown in FIG. 1 or makes use of a balun as shown in FIG. 2. The conventional basic measurement bridge 200 of FIG. 2 comprises a plurality of resistors 211 and a balun 210.

An example of a directional bridge and a balun scheme is illustrated in U.S. Pat. No. 4,962,359 to Dunsmore entitled "Dual directional bridge and balun used as reflectometer test set". According to Dunsmore there is provided a test set for use in measuring S-parameters with a network analyzer includes a first directional bridge, a second directional bridge and a single balun with two outputs mounted in an RF housing. A test signal from an RF signal source is transmitted through the test set to a device under test. The first directional bridge separates a signal from the device under test and the test signal, and provides the signal from the device under test to a coupled port. The second directional bridge separates the test signal and the signal from the device under test and provides the test signal to a reference port. The balun includes a coaxial transmission line with its outer conductor grounded at an intermediate location to define first and second balun sections. Ferrite beads are mounted on each of the balun sections. The ends of the first and second balun sections are coupled to the first and second directional bridges, respectively.

The disadvantage of applying the scheme disclosed by this publication is that it requires either magnetic components or large transmission line components to achieve broadband operation i.e. coupler or a balun for separating an input test signal to a device under test and a signal from the device under test.

It would therefore be desirable to provide an improved, cheap and compact device without requiring use of couplers (e.g. balun).

The term "Vector Network analyzer (VNA)" as used herein and through the specification and claims should be understood to encompass an electrical device used to generate and transmit RF signals and to measure the ratios between the received RF signals and the transmitted one. Those relations represent the reflection and transmission coefficients of the tested port.

The term "S-parameters" as used herein and through the specification and claims should be understood to encompass scattering parameters, e.g. the set of reflection and transmission coefficients of a system from each port to the other. Two ports "S-parameters" typically include 4 terms:
Port1 and port2 reflection coefficients (2 Terms)
Port1 to port2 and port2 to port1 transmission coefficients (2 Terms)

The term "T Parameters" as used herein and through the specification and claims should be understood to encompass scattering transfer parameters, which are another representation of the S-parameters, in which concatenation of 2-ports is translated into matrix multiplication of the corresponding T-parameter matrices of the corresponding 2-port elements.

The term "Antenna" as used herein and through the specification and claims should be understood to encompass an RF element used to transfer electrical RF signal (voltage and current) to propagating wave (electrical & magnetic fields).

The term bridge' as used herein and through the specification and claims should be understood to encompass a type of electrical circuit in which two circuit branches are "bridged" by a third branch connected between the first two branches at some intermediate point along them.

The term "balun" as used herein and through the specification and claims should be understood to encompass a device that joins a balanced line (one that has two conductors, with equal currents in opposite directions, such as a twisted pair cable) to an unbalanced line (one that has just one conductor and a ground, such as a coaxial cable).

SUMMARY OF INVENTION

According to a first aspect of the invention there is provided a directional bridge for characterizing a signal reflected from an RF device under test (DUT)) comprising: a differential signal source with two antipodal outputs wherein the first output is connected to a reference termination, and the second output is connected to the DUT, and at least one equal-ratio resistive divider wherein one side of the resistive divider is attached to the first output, and the second side of the resistive divider is connected to the second output and the middle point of the resistive divider is connected to a receiver, wherein said equal-ratio resistive divider is configured to provide a separated forward and reverse signals by canceling a differential mode of a transmitted signal at said bridge.

According to a second aspect of the present invention there is provided a network analysis directional bridge comprising: a plurality of resistors to provide a separated forward and reverse signals by canceling a common mode of a transmitted signal at said bridge; a differential input port and a reference receiver port; at least one deferential receiver, wherein said differential receiver arms are concocted to at least one of said plurality of resistors; and a single ended bridge output port connected to at least one of said plurality of resistors.

In an embodiment comprises a second equal-ratio resistive divider wherein one side of the resistive divider is attached to the DUT, and the second side of the resistive divider is connected to the reference termination and the middle point of the second resistive divider is connected to a second receiver input.

In an embodiment said second receiver is a differential receiver, wherein the middle points of the first and second resistive dividers are connected to the inputs of the differential receiver.

In an embodiment the plurality of resistors comprise six resistors wherein four of the resistors are connected in parallel to the other two resistors.

In an embodiment a test signal port connected via a signal splitter to the deferential receiver port arms, said test signal port is configured to receive a test tone to correct the differential receiver tracking.

In an embodiment said reference receiver port is a differential receiver port.

In an embodiment the bridge comprises a second test signal port connected via a second signal splitter to the deferential receiver port.

In an embodiment the test signal port is configured to pre-calibrate the bridge to correct the bridge and the receiver mismatch at an operational mode.

In an embodiment said plurality of resistors are symmetrically structured.

According to a third aspect of the present invention there is provided a network analysis directional bridge comprising: a differential receiver and a differential reference receiver; a plurality of resistors to provide two separated forward and reverse signals at said bridge by canceling a common mode of a transmitted signal; and a single ended input port connected to at least one of said plurality of resistors arms; a first test signal port connected via a first signal splitter to the differential receiver; a second test signal port connected via a second signal splitter to the deferential receiver port; and a single ended output port connected to at least one of said plurality of resistors.

According to a fourth aspect of the present invention there is provided a network analysis directional bridge comprising: a first unit comprising a plurality of resistors said first unit is coupled to a second unit said second unit comprising a plurality of resistors, and wherein said coupled units are configured to provide a separated forward and reverse signals by canceling a common mode of a transmitted signal at said bridge; an input port connected to said first unit; an output port connected to said second unit; a differential receiver unit connected to said first unit; and a differential reference receiver unit connected to said second unit.

In an embodiment each of said first and second unit comprises four resistors.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit.

BRIEF DESCRIPTION OF THE DRAWINGS

The subject matter disclosed may best be understood by reference to the following detailed description when read with the accompanying drawings in which.

DETAILED DESCRIPTION

The present invention relates to measurement device, system and method, more particularly to a balanced bridge unit, for example a balanced bridge unit in a vector network analyzers configured to produce signals proportional to an outgoing (e.g. transmitted) and incoming (e.g. received) signals at a VNA port.

The present invention further provides a VNA including a balanced bridge implemented for example at least in part within a printed circuit board (PCB) or chip.

According to some embodiments of the invention there is provided in a measurement system comprising a VNA and one or more resistors wherein the resistors are configured to separately measure a received and transmitted signal for identifying the coefficient reflection of a DUT.

The prior art solutions that are currently used to separately measure a received and transmitted signal (such as the VNA illustrated in FIG. 1) utilize one or more directional couplers such as passive directional coupler formed for example on a stripline circuit which uses a flat strip of metal sandwiched between two parallel ground planes. However, the limitation of this approach is that the lowest operational frequency of the coupler is related to its size, and typically will be on the order of 1 GHz or more.

Moreover, prior art solutions to increase the system's bandwidth by using wide bandwidth directional couplers with additional magnetic components, brought the low frequency cutoff to the MHz range, however this comes at expense of more bulky and expensive solution.

The present invention provide a system and method comprising at least one differential buffer (e.g. differential transmitter outputs or differential receiver inputs) for each VNA port, wherein the differential capability of the buffer is utilizes by a resistive bridge structure in order to produce signals proportional to the magnitude of the outgoing and the incoming signals at the VNA port.

According to some embodiments of the present invention, one of the differential through lines (Positive or Negative) is used as a referenced signal to the transmitter avoiding the need for additional components (such as directional couplers) at the through line.

As a result the following advantages are received:
Wide bandwidth, e.g. the present invention embodiment does not have a low frequency cutoff as it can effectively perform from DC. At the high end of the frequency the design is limited only by the transmitter BW and parasitics associated with the resistive implementation and the buffer (e.g. differential transmitter outputs or differential receiver inputs) differential accuracy;
The resistive design yields an inherently well matched implementation;
Minimal footprint—implementation is associated with the footprint of several resistors;
Low cost;
High directivity of the bridge. By utilizing CMMR as an isolation mechanism, we attain good separation of the incoming signal from the outgoing signal; and
By employing also the isolation (DUT port to REF) improvement, one can attain even higher isolation between the DUT port and reference receiver. Moreover, one can then, decouple insertion loss from this isolation.

In other words, the present invention utilize the differential signals provided by a microwave system to provide a unit configured to separate the transmitted and reflected signals therefore enabling to minimize the lowest frequency to zero without increasing the system physical size and complexity.

According to one embodiment of the invention there is provided a test set comprising a balanced bridge, the balanced bridge comprises a plurality of resistors to provide a separated forward and reverse signals by canceling a common mode of a transmitted signal at said bridge.

In another embodiment of the invention, in order to enhance the bridge RX and reference directivity a number of calibration steps are provided. In a first calibration step the imbalance factors for the RX and the reference finite directivity (due to implementation limitation) are measured and then used to correct the RX and reference inherent finite directivity In a second calibration step, the two reference receivers and the two RX receivers tracking deviation over temperature is corrected by inserting a test tone to the correspondence P/N ports of the dual receivers (as the P/N ports of the receivers have the best tracking performances over temperature) to correct the two differential receivers tracking. For example, a test tone is inserted to the other port of the two receivers (p or n) via a power splitter and the value of the ratio of the two receivers is recorded.

Figure 3A:
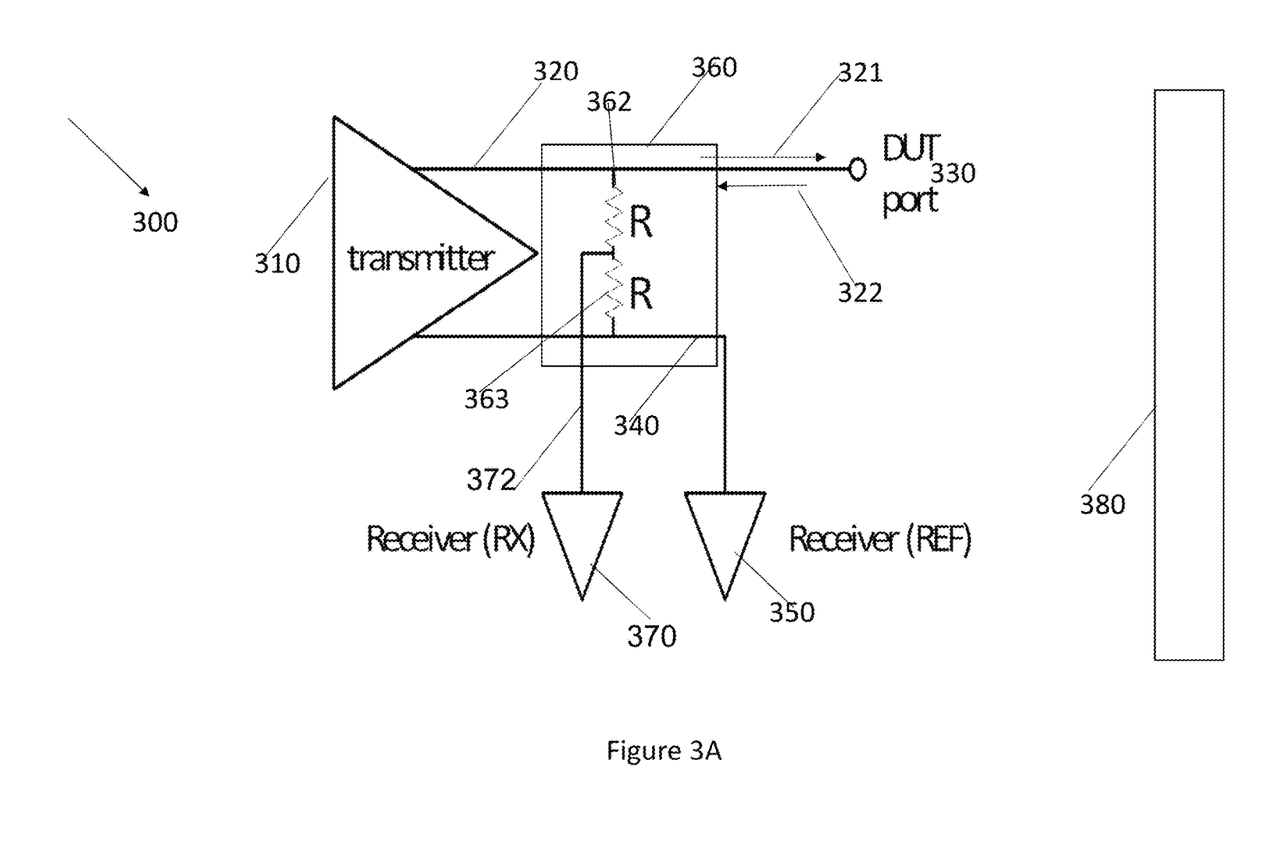
FIGS. 3A and 3B—show a number of simplified block diagrams of a balanced bridge, constructed according to the principles of the present invention.

Reference is now made to FIG. 3A illustrating a VNA scheme 300 according to one embodiment of the invention. The scheme includes at least one transmitter 310 connected via line 320 (i.e. upper line) to a VNA port 330 and via line 340 (i.e. lower line) to a Reference Receiver 250 (REF). The system further includes a Differential Bridge Unit (DBU) 360 including a plurality of resistors such as resistors 362 and 363 connected in series to the upper line 320 and the lower line 340. The system further includes a Receiver 370 connected via line 372 to the DBU 360.

Upon activation, two signals run simultaneously on line 320: a transmitted signal and a reflected signal 322 received for example from DUT 380. Therefore, each point on line 320 accumulates a Voltage resulted from both the transmitted (i.e. forward) and reflected signal while the lower line 340 comprises only the transmitted signal (as line 340 is not connected to the VNA port 330 it doesn't include the reflected signal).

The two resistors 362 and 363 included in the DBU 360 are configured to calculate an averaged signal received between the upper line 320 and the lower line 340. As both the upper and lower lines include the transmitted signal in an opposite phase and in an opposite polarity the transmitted signal are averaged to zero while the received signal will not be averaged and interfered by the transmitted signal 321 and received separately by receiver 370.

Figure 3B:
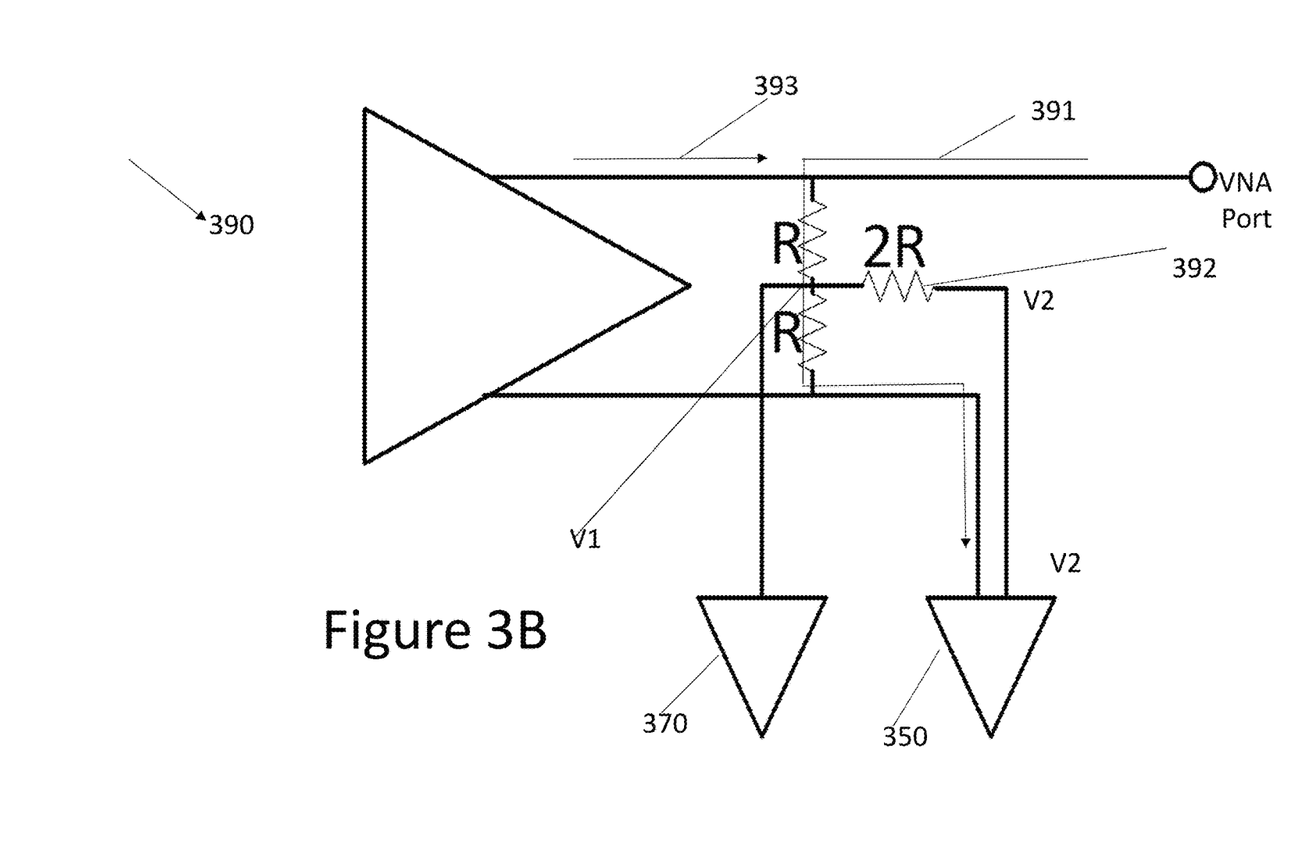

Reference is now made to FIG. 3B illustrating a measurement system scheme 390 according to another embodiment of the invention. To avoid the effect of an 'unwanted' reflected signal 391 (measured for example at V1) at REF Receiver 350, one or more resistors 392 (i.e. two resistors) are added to the Differential Bridge Unit, configured to cancel the 'unwanted' effect of signal 391 and therefore produce a scaled transmitted signal proportional to the outgoing signal 393 transmitted from the transmitter 310.

Figure 4:
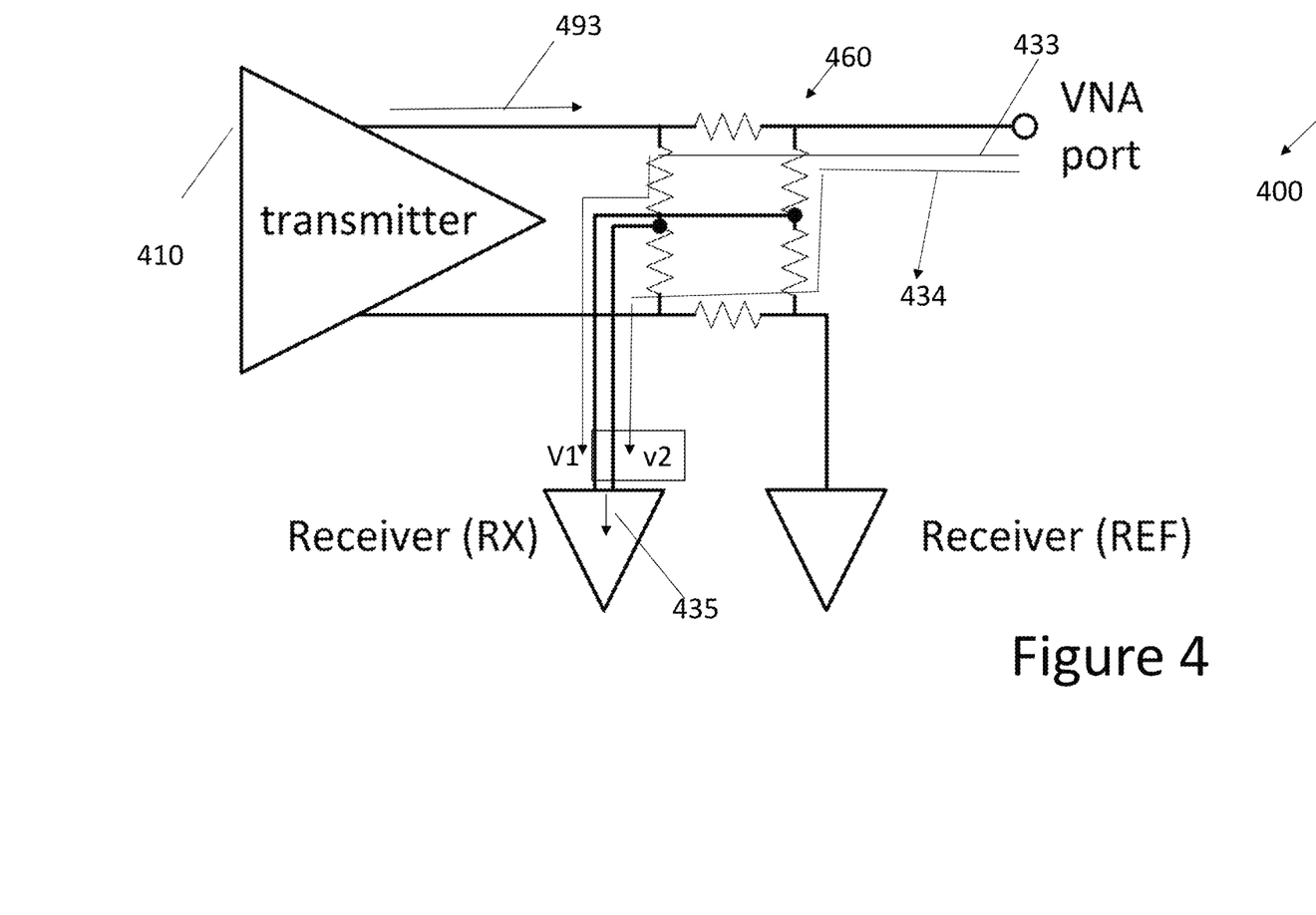
FIGS. 4 and 5 show a balanced bridge, according to another embodiment of the present invention.

FIG. 4 illustrates another embodiment according to the present invention, wherein a balanced bridge unit 460 further includes a plurality of resistors configured to scale the non-deferential characteristic of the transmitter and therefore produce a transmitted signal proportional to an outgoing signal 493 transmitted from the transmitter 410. In other words as an 'unwanted' reflected signal is received at point V1 and another signal 434 is scaled at point V2 resulting at a transmitted signal 435 (e.g. V1-V2).

Figure 5:
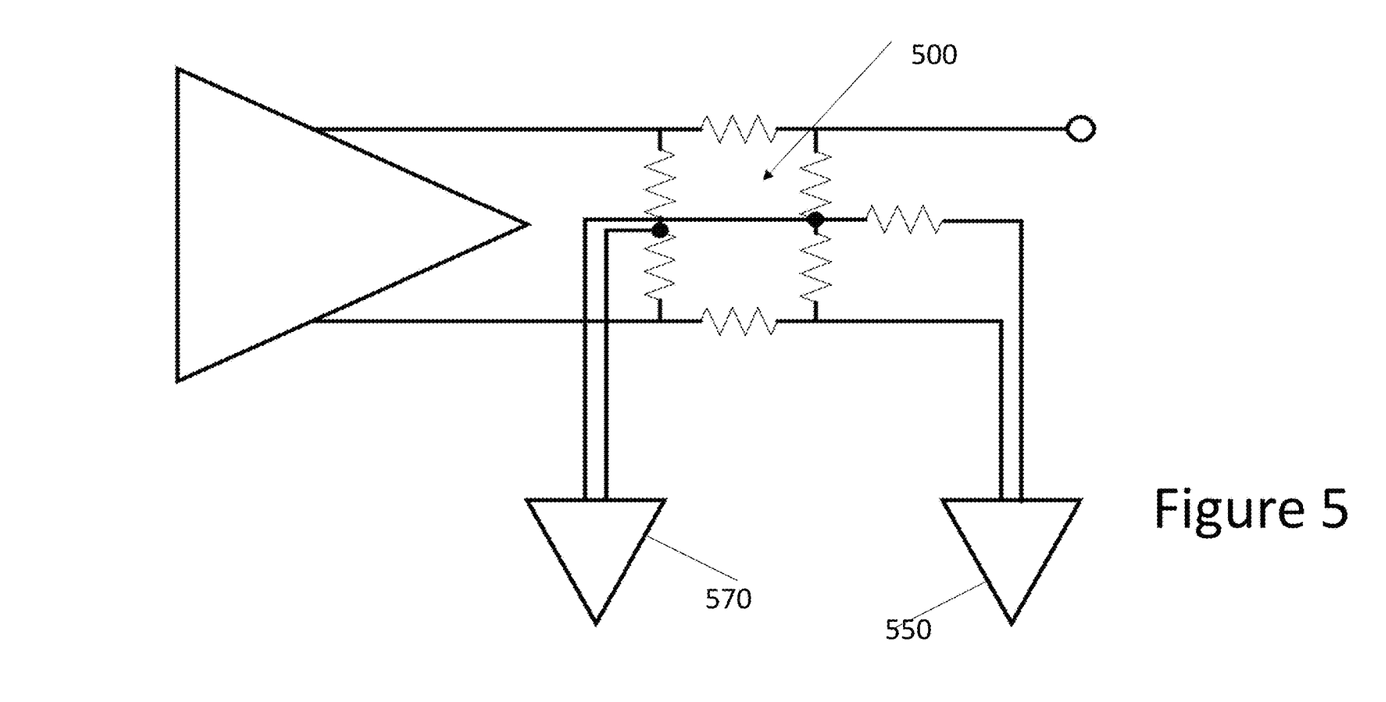

FIG. 5 illustrates another embodiment comprising a Balanced Bridge Unit 500 configured to scale both the unwanted reflected signals at Receiver RX 570 and REF receiver 550.

Figure 6A:
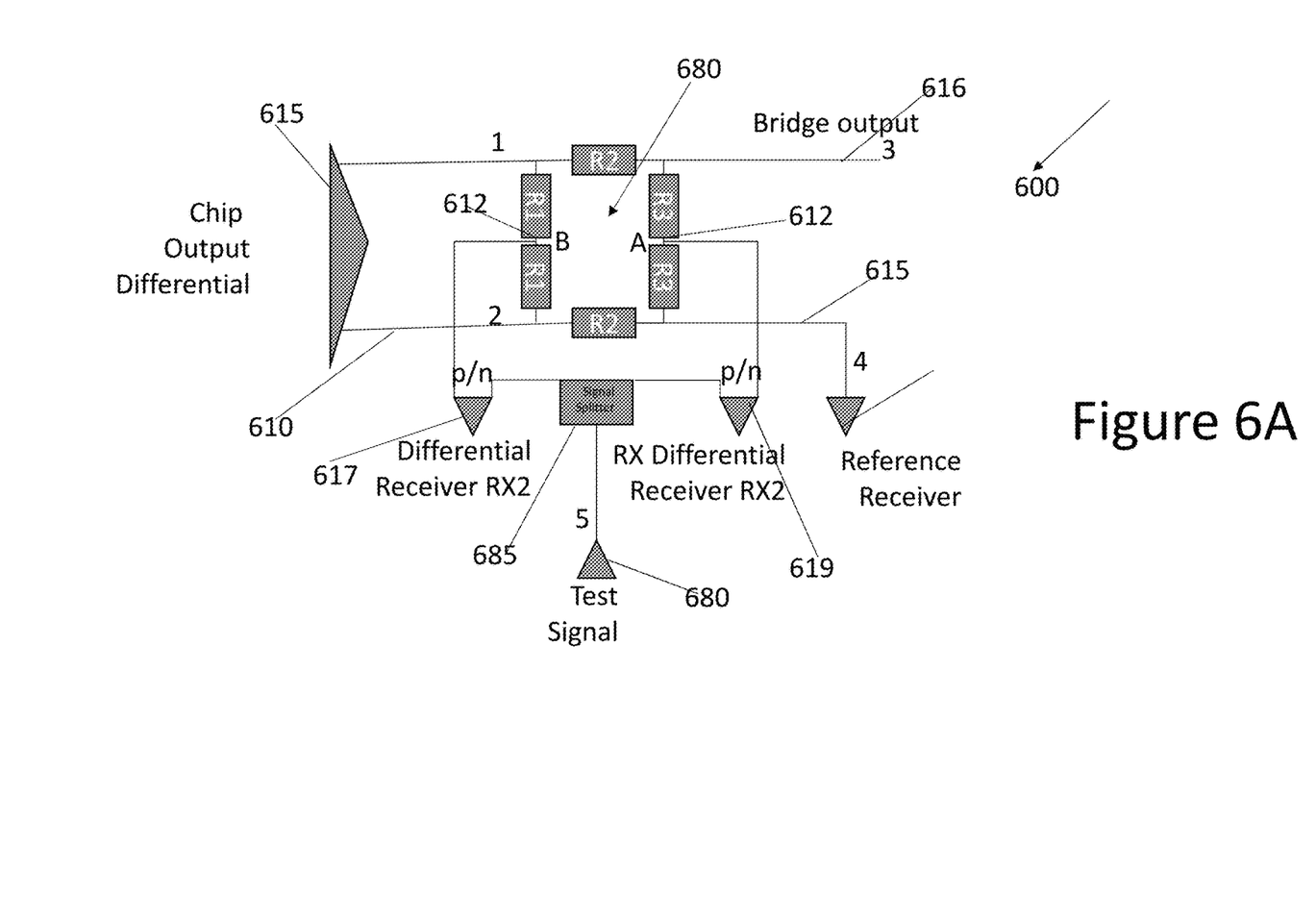
FIGS. 6A and 6B show a number of simplified block diagrams of a balanced bridge including a balance input to single ended output bridge, constructed according to the principles of the present invention.
Figure 6B:
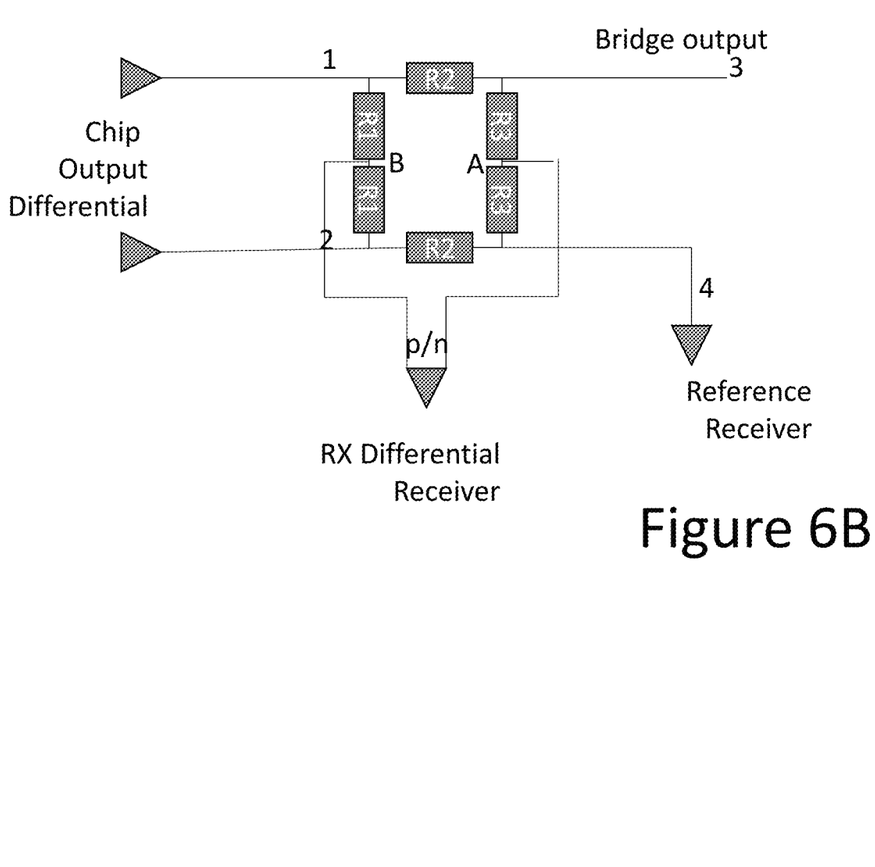

Reference is now made to FIG. 6 which illustrates a test set 600 comprising a balance input to single-ended output bridge 680 according to one embodiment of the present invention. The test set 600 comprises: a differential bridge input port 610 configured to be connected to a differential source (e.g. chip) output port 615, a single ended bridge output port 616 (e.g. bridge test port) configured to be connected to a DUT port, a differential Rx receiver 617 and a single ended reference receiver 619. The bridge 680 further comprises a plurality of resistors 660 configured to provide a separated forward and reverse signals at said bridge (e.g. at points 613) by canceling a common mode signal of a transmitted signal. The common mode cancelation is achieved by the symmetrical resistors scheme and since the bridge RX outputs 612 ports are fed into a differential receiver As illustrated in FIG. 6 the bridge 680 comprises three pairs of resistors R1, R2 and R3. The resistors values of R1, R2 and R3 are designed so as the resulted transfer function from the bridge input port 610 to ports 312 (points A and B) is identical. On the other hand, the transfer functions from port 3 (e.g. output port 616) to ports 612 (points A and B) are not equal and therefore the reflected power when the load is not matched for example to 50 ohm is not cancelled. The cancellation of the common mode is achieved by connecting ports 612 (points A and B) to a differential receiver 617. The common mode quality cancelation depends on the bridge 680 symmetric quality (implementation limitation) and RX receiver differential quality. In should be noted that cancellation of the common mode as achieved and illustrated in FIG. 6 is true for the following figures.

Figure 7:
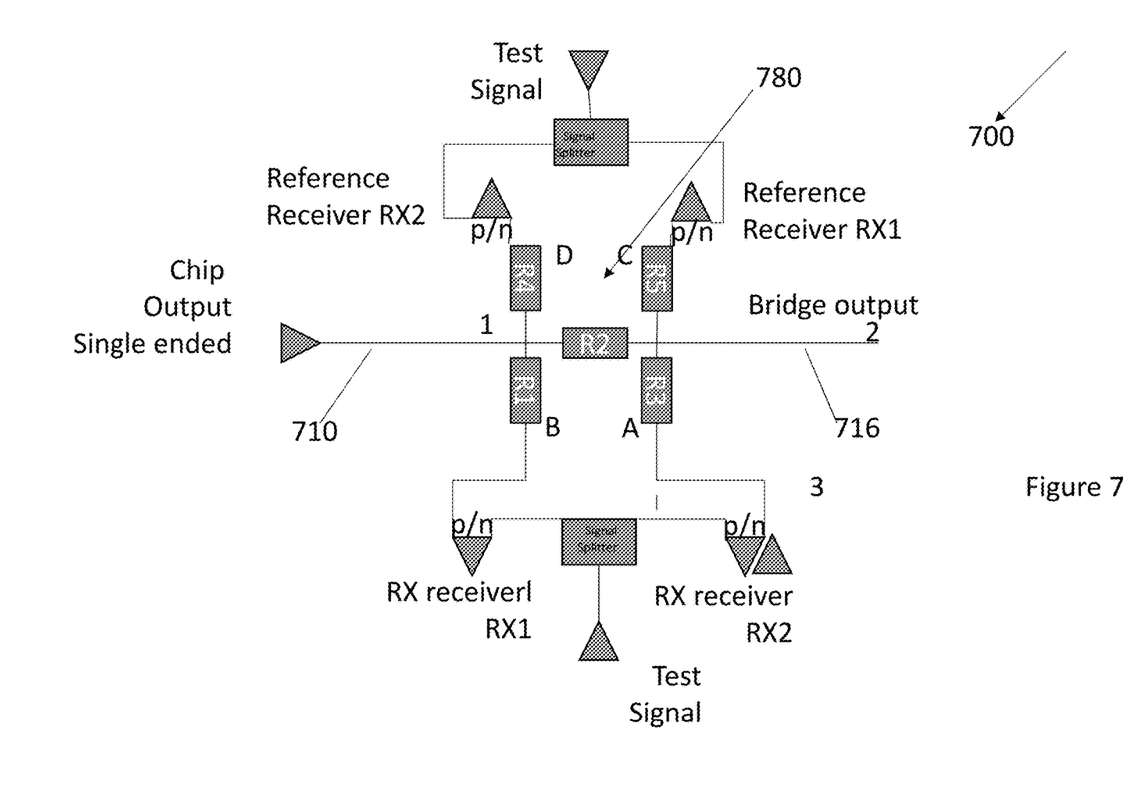
FIG. 7 show a simplified block diagrams of a single ended to single ended bridge calibrated, constructed according to the principles of the present invention.

While FIG. 6 illustrates a scheme that doesn't include a calibration step, FIG. 7 provides an alternative scheme which provides an enhanced RX directivity, by overcoming implementation limitation utilizing two differential RX receivers.

Reference is now made to FIG. 7 illustrating a test set 700 comprising a bridge 790 according to another embodiment of the present invention. As explained hereinabove the present invention provides a device and method for canceling the device's common mode signal (since the bridge and the receivers are not perfectly matched). FIG. 7 provides a device and method for canceling a common mode signal leftover by measuring the common mode at points 705 and further canceling the measured common mode. In other words, the balanced bridge 790 as illustrated in FIG. 7 is an input to single-ended output bridge configured to calibrate the test set 700 RX directivity prior to a complete test set calibration.

The bridge 790 comprises: a differential bridge input port 710 configured to be connected to a differential source (e.g. chip) output port, a single ended bridge output port 716 (e.g. bridge test port) configured to be connected to a DUT port, a differential Rx1 receiver 717, a differential Rx2 receiver 719 and a single ended reference receiver 719. The bridge further comprises a plurality of resistors 760 configured to provide a separated forward and reverse signals at said bridge by canceling a common mode signal of a transmitted signal. As illustrated in FIG. 7 the bridge 780 comprises three pairs of resistors R1, R2 and R3. The resistors values of R1, R2 and R3 are designed so as the resulted transfer function from the bridge input port 710 to the points A and B (712) is identical. On the other hand, the transfer functions from port 3 (e.g. output port 716) to points A and B are not equal and therefore the reflected power when the load is not matched for example to 50 ohm is not cancelled According to some embodiments of the invention, the bridge 790 common mode signal is transformed to a common mode of the dual receivers input (e.g. 717 and 719) and subtracted digitally in order to enhance the bridge directivity. The imbalance of the two receivers 717 and 719 and the bridge is pre-calibrated in order to achieve perfect subtraction and isolation from device input to the subtracted signals. This step is performed by transmitting a test signal into matched load (at the bridge output 715 for example 50 ohm) and recording the signals at RX receivers RX1 and RX2. The ratio of the signals (amplitude and phase) is the imbalance factors of the two receivers 717 and 719 and the bridge. These imbalance factors are used to correct for the finite RX directivity of the bridge during the VNA system calibration process and during the operation mode.

According to another embodiment of the invention, to improve the two receivers tracking over temperature a test tone 780 may be inserted to the other port of the two receivers (p or n) via a power splitter 785 and the value of the ratio of the two receivers 717 and 719 is recorded. This step may be done in parallel to the mismatch calibration process described herein above and may be used as a reference value to the receivers tracking. As the design of the p and n ports of a single receiver is in very good tracking over temp, the actual receivers tracking over temp is improved.

Reference is now made to FIG. 7 which illustrates a test set 500 comprising a balanced bridge 780 according to another embodiment of the present invention. The bridge 780 comprises a single-ended input port to single-ended output port and the bridge RX arms as well as the reference arms comprise duel differential receivers.

The bridge 780 comprises, for example five resistors R1-R5 wherein the resistors values of R1, R2 and R3 are designed so as the resulted transfer function from the bridge input port 710 to the points A and B is identical. On the other hand, the transfer functions from port 2 (e.g. output port 716) to points A and B are not equal and therefore the reflected power when the load is not matched for example to 50 ohm is not cancelled. The output of the RXs receivers are digitally subtracted and the chip output signal leakage is cancelled.

Additionally, the resistors values of R4 and R5 are designed so the transfer functions from bridge output to the points C and D are identical. As a result the reflected signal at points C and D appears equally (amplitude and phase). On the other hand, the transfer functions from port 1 to C and D are not equal and therefore the transmission power is not cancelled. The output of the Reference receivers are digitally subtracted and the reflected power from the load is cancelled In operation, the device's 700 output is sampled by the two differential reference receivers and the reflected signal is subtracted digitally in order to enhance the bridge reference directivity. The reflected signal is sampled by the two differential RX receivers and the forward signal is subtracted digitally in order to enhance the bridge RX directivity.

In the following step, the imbalance of the two RX receivers, the two reference receivers and the bridge may be pre-calibrated in order to improve RX and reference directivity. The Rx pre calibration step is done by transmitting into matched load (e.g. at the bridge output for example 50 ohm) and recording the signals at RX receivers RX1 and RX2. The ratio of the signals (amplitude and phase) is the imbalance factor of the two receivers and the bridge. These imbalance factors are used to correct for the finite RX directivity of the bridge during VNA system calibration process and during the operation mode. In order to calibrate the reference directivity a test tone signal is transmitted through the Rx2 transceiver, while the output of the bridge is terminated by a match load. The leakage of reflected test signal is recorded at the reference receiver Rx1 and Rx2. The ratio of the recorded leakage signal at the reference receiver Rx1 and Rx2 (amplitude and phase) is the imbalance factor of the two reference receivers and the bridge. These imbalance factors are used to correct for the finite reference directivity of the bridge during VNA system calibration process and during the operation mode.

In the next step, the two RX receivers and the two reference receivers tracking deviation over temperature is corrected by inserting a test tone to the correspondence P/N ports of the dual receivers (as the P/N ports of the receivers have the best tracking performances over temperature) to correct the two differential receivers tracking. For example, a test tone is inserted to the other port of the two receivers (p or n) via a power splitter and the value of the ratio of the two receivers is recorded.

Figure 8:
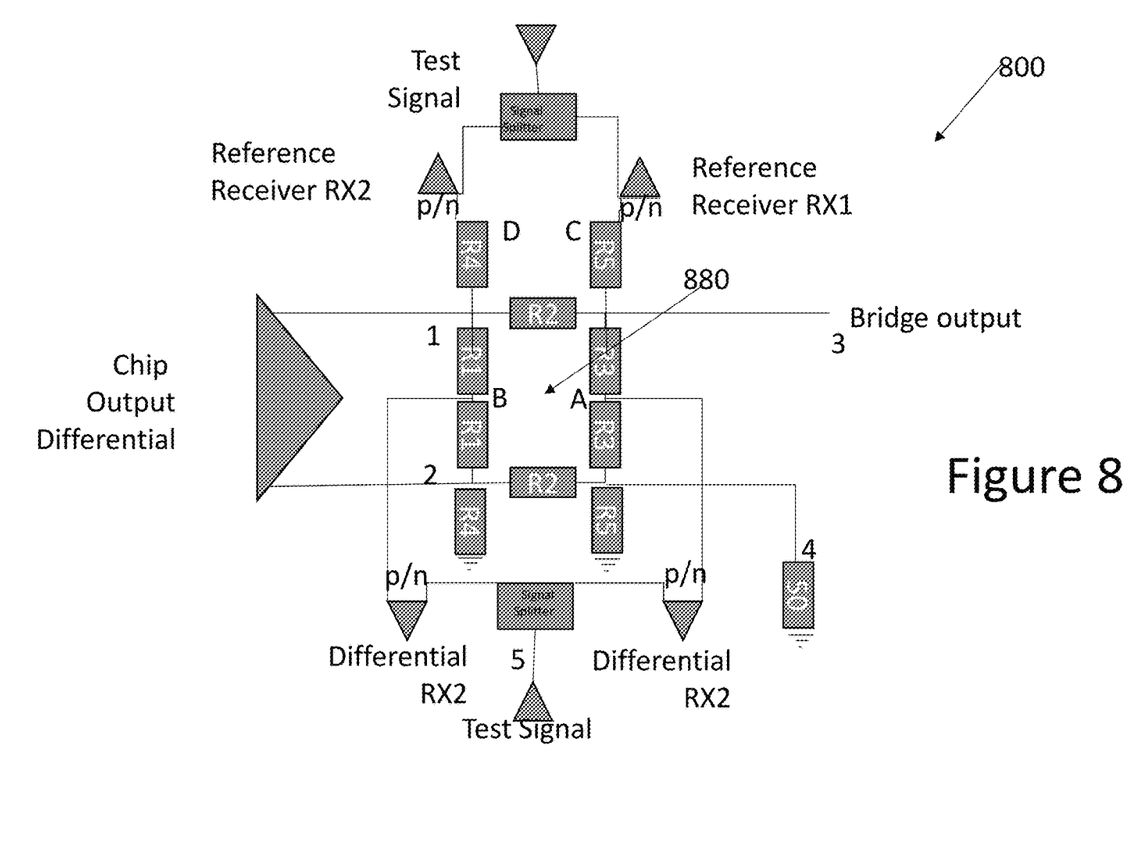
FIG. 8 show a simplified block diagrams of a balance input to single ended output bridge and reference calibrated version, constructed according to the principles of the present invention.

Reference is now made to FIG. 8 which illustrates a test set 800 comprising a balanced bridge 880, according to another embodiment of the present invention. The bridge scheme 880 is based on the scheme 580 shown in FIG. 7, however according to scheme 680 the input to the bridge is balanced and the output is single-ended. The input signal to the RX receivers (points A and B) are the common mode of the transceiver and may therefore be suppressed.

Bridge to Bridge Coupling

Traditional couplers which are based on resistor bridge typically require at least one of the bridge ports to be floating, e.g. not sharing the same ground as other ports. Additionally, traditional VNA requires two chained couplers, a first coupler for a reference (forward) signal and a second coupler Rx (backward reflection) signal.

The present invention provides a device and method comprising cascading two bridge couplers to one another, so that the floating output of the first bridge coupler will be the differential input of the second bridge coupler.

Figure 9:
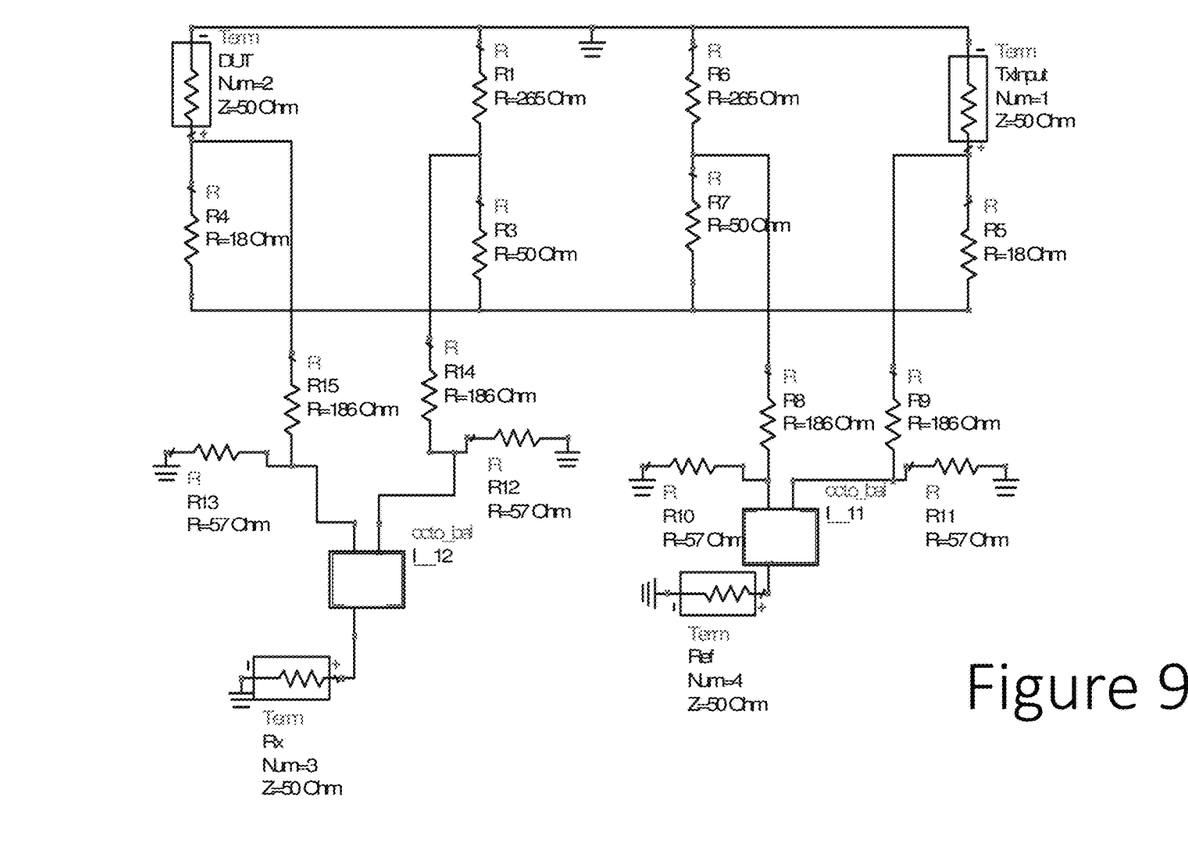
FIG. 9 show a simplified block diagrams of a bridge to bridge coupler, constructed according to the principles of the present invention.

Reference is now made to FIG. 9 which illustrates test set 900 comprising two bridge 910 and 920 which are cascaded to one another, according to some embodiments of the present invention. According to the test set 900 scheme a Tx and DUT ports are single ended and the reference and Rx are differential. For example, the single ended ports may be matched to 50 ohm, and the differential ports to 100 ohm.

A condition equation for the bridges balance may be as follows:

$$RTx/R5=R6/R7=R1/R3=Rdut/R4$$

And the coupling and loss of the test set 900 may be determined by R4.

Figure 10:
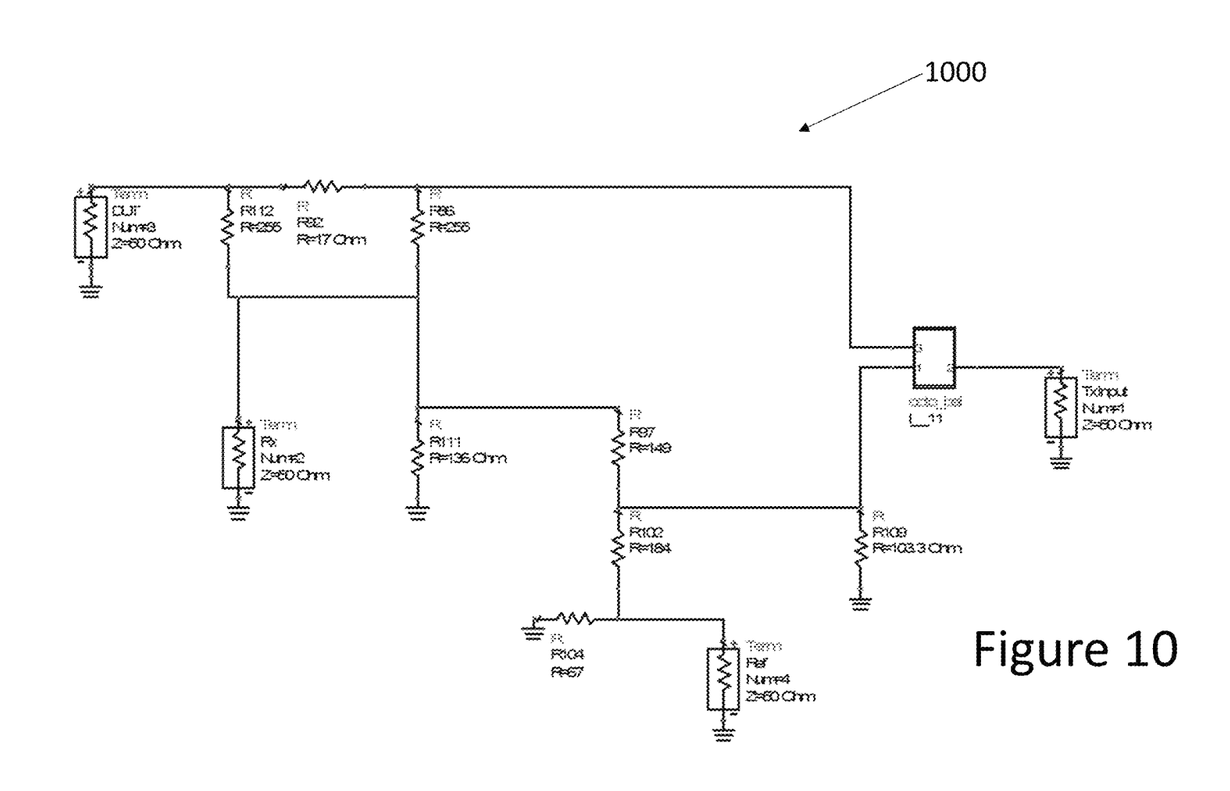
FIG. 10 show a simplified block diagrams of a single ended active bridge coupler, constructed according to the principles of the present invention.

Reference is now made to FIG. 10 which illustrates a test set 1000 comprising a SE (singled ended) matched active bridge coupler, according to some embodiments of the present invention. Generally, IC's (Integrated Circuit) differential RF outputs/inputs are not floating but have impedance to ground (usually 50 Ohm). As a result, implementing active differential TR yields a problem when utilizing a resistor bridge as the bridge requires floating ports.

The test set 1000 provides a scheme which has the properties of bridge resistors in terms of loss and coupling and is matched to, for example 50 ohm in each port (including differential). Additionally, the device 1000 combines an optional reference output enabling the use as source tracking reference and may eliminate the need for additional couplers.

Figure 11:
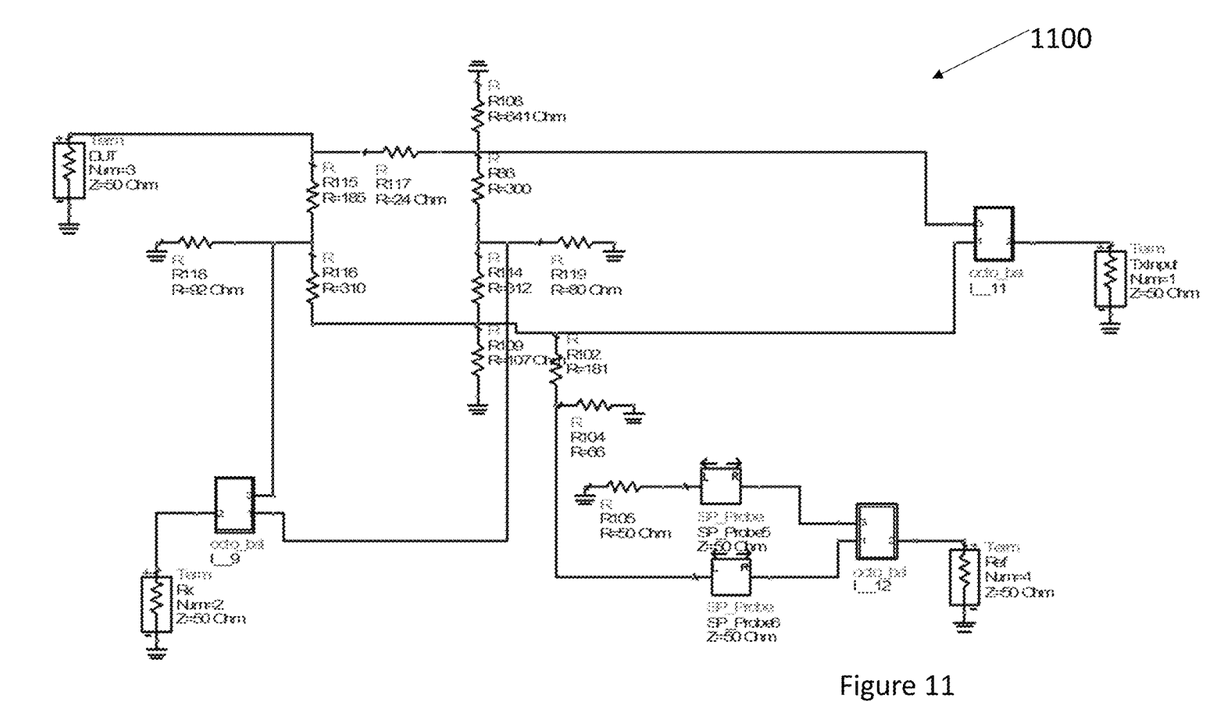
FIG. 11 show a simplified block diagrams of a single ended matched active bridge coupler, constructed according to the principles of the present invention.

The test set 1000 comprises a DUT port and Rx port and source tracking reference ports which are all single ended. The device further comprises a differential Tx port where each of the port's line impedance to ground is 50 ohm. In an embodiment, all the device's ports are matched to 50 ohm and the loss and coupling of the reflected signal is determine by R17 (e.g. typical values can be 3 db loss and 15 db coupling). Reference is now made to FIG. 11 which illustrates a test set 1100 configured to provide larger loss per fixed coupling. According to some embodiments of the present invention the test set 1100 comprises Diff-Diff SE matched active bridge coupler. The coupler comprises Tx and Rx differential ports which are related to the ground and are utilized to improve the coupler immunity to differentially mismatch of the ports.

The test set 1100 comprises a single ended DUT, Rx and source tracking reference ports and a differential Tx port where is each of the TX port through line impedance to the ground is 50 ohm. Additionally, as in the hereinabove schemes the ports are matched to 50 ohm and the loss and coupling is determine by R17 (for example 4.2 db and 21 db).

To summarize, the present invention embodiments are based on the following:
1. The utilization of both Negative and Positive channels of a differential transmitter as two well matched transmitters.
2. The usage of Common Mode Rejection Ratio ('CMRR' between differential and common modes) of an isolation mechanism.
3. Improvement of port to REF isolation by means of common mode cancelation
4. The tracking of the P/N sides of the balanced transmitter facilitate the usage of one as a reference to the other, which drives the DUT.

The terms "comprises", "comprising", "includes", "including", "having" and their conjugates mean "including but not limited to". This term encompasses the terms "consisting of" and "consisting essentially of".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A directional bridge for characterizing a signal reflected from an RF device under test (DUT) comprising at least two equal-ratio resistive dividers, wherein said directional bridge is connected to a differential signal source with two antipodal outputs, wherein the first antipodal output is connected to a reference receiver, and the second antipodal output is connected to the DUT, and wherein one side of a first one of the at least two equal-ratio resistive dividers is attached to the first antipodal output, and a second side of the first one of the at least two equal-ratio resistive dividers is connected to the second antipodal output, and the middle point of the first one of the at least two equal-ratio resistive dividers is connected to a first input of a differential receiver, and wherein one side of a second one of the at least two equal-ratio resistive dividers is attached to the DUT, and a second side of the second one of the at least two equal-ratio resistive dividers is connected to the reference receiver, and the middle point of the second one of the at least two equal-ratio resistive dividers is connected to a second input of said differential receiver.

2. The directional bridge of claim 1, wherein said reference receiver is a differential receiver, and the second input of said reference receiver is connected to the middle of said second equal-ratio resistive divider.

3. A network analyzer comprising the directional bridge of claim 1.

4. A network analyzer comprising the directional bridge of claim 2.

* * * * *